United States Patent [19]
Vinot

[11] Patent Number: 5,459,079
[45] Date of Patent: Oct. 17, 1995

[54] SUPPORT FOR BIOLOGICALLY ACTIVE MOLECULES WHICH ITSELF MAY BE BIOLOGICALLY ACTIVE, PROCESS FOR ITS PREPARATION AND ITS BIOLOGICAL APPLICATIONS

[75] Inventor: Bernard Vinot, Paris, France

[73] Assignee: Rhone-Poulenc Chimie, Courbevoie, France

[21] Appl. No.: 206,215

[22] Filed: Mar. 7, 1994

Related U.S. Application Data

[63] Continuation of Ser. No. 425,060, Oct. 20, 1989, abandoned.

[30] Foreign Application Priority Data

Oct. 21, 1988 [FR] France ................... 88 13798

[51] Int. Cl.⁶ ............. G01N 33/543; G01N 33/545; G01N 33/546
[52] U.S. Cl. ............... 436/518; 422/56; 422/57; 436/170; 436/531; 436/532; 436/533; 436/534; 436/807; 436/810
[58] Field of Search ............... 428/403, 407; 422/56, 57; 436/518, 531, 532–534, 170, 807, 810; 525/54.1, 329.5, 329.7, 330.3, 333.3; 526/318.1, 329.7, 346

[56] References Cited

U.S. PATENT DOCUMENTS

| | | | |
|---|---|---|---|
| 3,857,931 | 12/1974 | Hager | 424/12 |
| 4,045,384 | 8/1977 | Dorman | 424/88 |
| 4,046,723 | 9/1977 | Dorman | 424/12 |
| 4,071,409 | 1/1978 | Messing et al. | 195/63 |
| 4,140,662 | 2/1979 | Reckel et al. | 424/12 |
| 4,218,363 | 8/1980 | Rohrbach et al. | 260/42.14 |
| 4,268,423 | 5/1981 | Rohrbach et al. | 252/430 |
| 4,337,172 | 6/1982 | Teague et al. | 252/430 |
| 4,340,564 | 7/1982 | Harte et al. | 422/57 |
| 4,352,884 | 10/1982 | Nakashima et al. | 435/180 |
| 4,421,896 | 12/1983 | Dorman | 435/181 |
| 4,670,381 | 6/1987 | Frickey et al. | 422/56 |
| 4,681,870 | 7/1987 | Balint, Jr. et al. | 210/263 |
| 4,762,787 | 8/1988 | Balint | 436/527 |
| 4,801,449 | 1/1989 | Balint, Jr. et al. | 436/527 |
| 4,820,633 | 4/1989 | Herrmann | 436/531 |
| 4,861,552 | 8/1989 | Masuda et al. | 436/501 |
| 4,868,106 | 9/1989 | Ito et al. | 436/527 |
| 4,960,692 | 10/1990 | Lentrichia et al. | 436/518 |
| 4,962,154 | 10/1990 | Pollock et al. | 525/54.1 |

FOREIGN PATENT DOCUMENTS

| | | |
|---|---|---|
| 1076502 | 4/1980 | Canada. |
| 2004892 | 4/1979 | United Kingdom. |

*Primary Examiner*—David Saunders
*Assistant Examiner*—Christopher L. Chin
*Attorney, Agent, or Firm*—Finnegan, Henderson, Farabow, Garrett & Dunner

[57] ABSTRACT

A support for biological molecules comprising a porous inorganic matrix and particles of a water-insoluble polymer, and a biologically active support comprising a porous inorganic matrix and particles of a water-insoluble polymer "sensitized" by biological molecules. The supports are prepared by bringing the matrix into contact with an aqueous dispersion of optionally "sensitized" polymer particles, and the use of such supports in biological application.

14 Claims, 1 Drawing Sheet

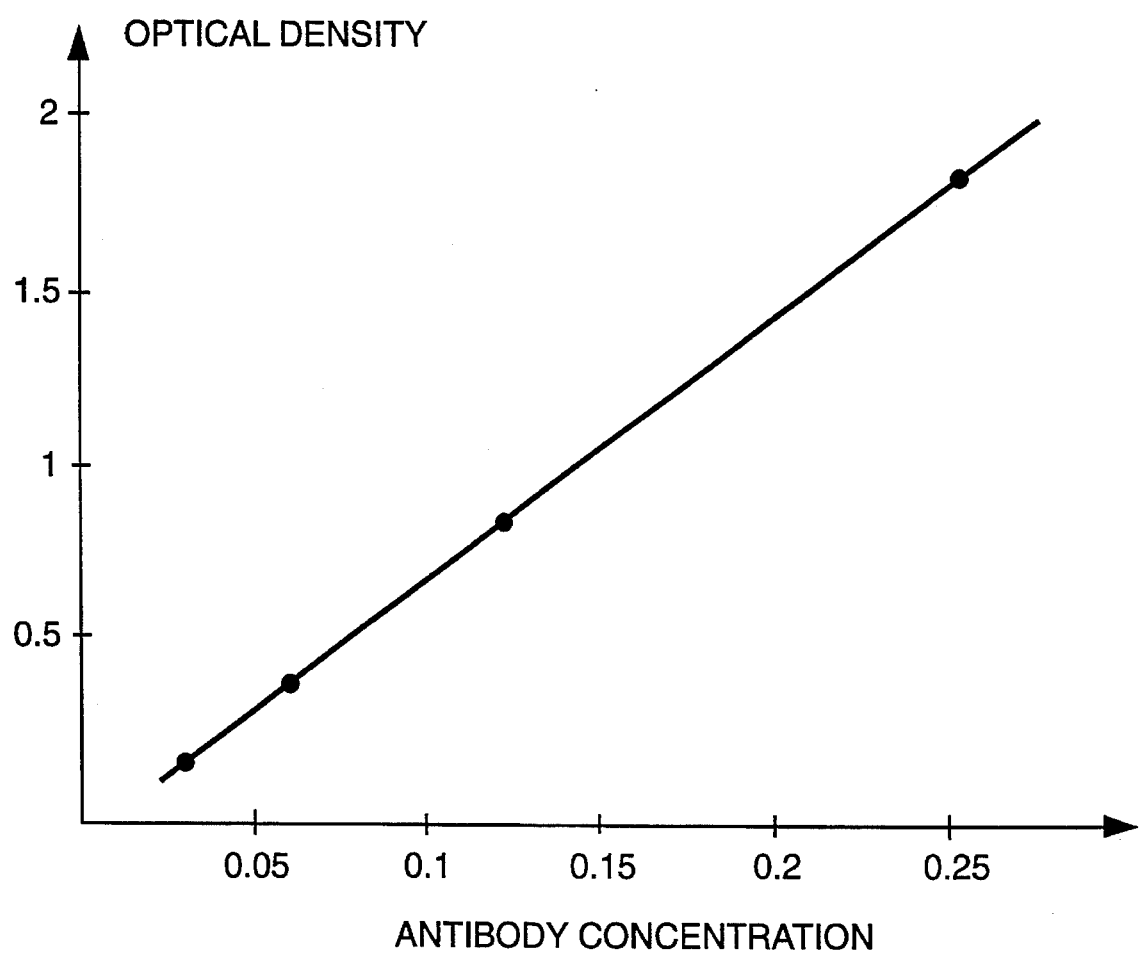

SUPPORT FOR BIOLOGICALLY ACTIVE MOLECULES WHICH ITSELF MAY BE BIOLOGICALLY ACTIVE, PROCESS FOR ITS PREPARATION AND ITS BIOLOGICAL APPLICATIONS

This application is a continuation of application Ser. No. 07/425,060, filed Oct. 20, 1989, now abandoned.

BACKGROUND OF THE INVENTION

The present invention relates to a support for biologically active molecules which itself may be biologically active, to the process for its preparation and to its use in biological applications such as affinity chromatography, diagnostic tests, and cell culture.

It is known to fix biologically active molecules onto polymer particles in an aqueous dispersion by adsorption when, for example, polystyrene particles are involved, or by covalency when polymers containing reactive groups are involved.

The advantage offered by latex lies in the large specific surface area developed by the particles and in the wide range of chemical functional groups which are available. Their disadvantage, on the other hand, lies in the difficulty of employing them, once atomized, as a packing system in columns or capillaries; in fact, when the diameter of the poller particles is less than 1 micron, the packing system obtained lacks permeability.

BRIEF DESCRIPTION OF THE DRAWINGS

FIG. 1 shows a calibration curve of optical density vs antibody concentration.

The applicant has found a support for biologically active molecules or which is itself biologically active which can be used as a packing system which is both permeable and of high specific surface area.

The support for biologically active molecules, forming the subject of the invention is characterized in that it comprises:
  a porous, water-insoluble inorganic matrix, and
  water-insoluble polymer particles on the surface of said matrix, which are capable of fixing biologically active molecules.

The term "surface area" means both the external surface area of the matrix and its internal surface area, that is to say that developed by the pores.

Any porous, water-insoluble inorganic materials may be used for the matrix. Preferably, the inorganic materials are selected from the group consisting of silicas, aluminas, zeolites, brick, titanium and zirconium oxides and porous glasses.

Silicas and aluminas are most preferably employed. The material of which the matrix consists may optionally have on its surface functional groups such as —COOH, —NH$_2$, —OH, —SH, etc. which are capable of reacting covalently with the polymer particles.

According to the invention, the matrix may have a pore volume in the order of about 0.5 to 1.8 ml/g, a pore diameter in the order of 0.005 to 10 microns, preferably of about 0.1 to 1 micron, and a specific surface area in the order of 2 to 1,000 m$^2$/g.

The matrix is preferably in the form of particles, more preferably in the form of beads, which have a diameter in the order of about 4 microns to 5 mm, preferably of about 50 to 500 microns.

A "water-immiscible monomer" means monomers which have a solubility of less than 5% by weight in water.

Among those which can be mentioned without limitation are:
  vinylaromatic monomers (styrene, vinyltoluene, etc.)
  alkyl esters of α, β-unsaturated acids (methyl, ethyl, acrylates and methacrylates)
  esters of unsaturated carboxylic acids (vinyl acetate, etc.)
  vinyl chloride, vinylidene chloride
  dienes (butadiene, etc.)
  those containing nitrile functional groups (acrylonitrile, etc.)
  siloxanes.

The monomeric composition from which the said polymer is derived may additionally contain up to about 10% of its weight (preferably up to about 4% of its weight) of at least one monomer bearing ionizable or reactive groups such as: —SO$_3$H, —OSO$_3$H, —NR$_3^+$, —COOH, —OH, NH$_2$, —NR$_2$,

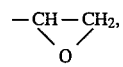

—φCH$_2$Cl, —CONH$_2$, —SH, , —COOR, —PO(OR)$_2$, R denoting a C$_1$-C$_4$, preferably C$_1$-C$_2$, alkyl radical.

By way of example there may be mentioned:
  vinylbenzene sulphonate, sulphoalkyl esters of unsaturated acids (2-sulphoethyl methacrylate, etc.)
  unsaturated carboxylic acids (acrylic, methacrylic, maleic, itaconic acids, etc.)
  hydroxyalkyl acrylates or methacrylates (hydroxyethyl, hydroxypropyl, etc., acrylate)
  aminoalkyl esters of unsaturated acids (2-aminoethyl methacrylate, etc.)
  acrylamide
  vinylbenzene chloride
  glycidyl methacrylate.

The polymer particles may have a particle size in the order of about 0.05 to 20 microns and preferably in the order of about 0.1 to 3 microns. Most preferably, the diameter of the polymer particles is smaller than that of the pores of the matrix, and most preferably smaller than 1 micron.

The weight of the matrix corresponds to approximately 1 to 1,000 times that of the polymer particles, more preferably approximately 50 to 500 times.

The support for biologically active molecules, which forms the subject of the present invention, may be prepared by "deposition" of the polymer particles on the surface of the matrix merely by contact of an aqueous dispersion (latex) of polymer particles with the porous matrix, followed by drying. Optionally one may wash with distilled water prior to drying. The latex used contains approximately 0.1 to 50% by weight of polymer particles, although it is preferable to use approximately 0.5 to 15% by weight.

The relative quantities of matrix and of aqueous dispersion which are used correspond to a matrix/polymer particles weight ratio in the order of 0.01 to 1,000; depending on the concentration of the dispersion and the physical characteristics of the matrix, the quantity of particles used corresponds to approximately 1 to 100 times that deposited.

The unused dispersion can be reused in a subsequent operation, after separation of the support obtained.

When the support is prepared from a matrix whose surface has functional groups capable of reacting covalently with the polymer particles, it is preferable to preactivate the matrix with the aid of a coupling agent such as a water-soluble carbodiimide, glutaraldehyde, N-hydroxybenzenetriazole, cyanogen bromide, etc., and then to place it in contact with the polymer dispersion.

The support described above may be employed for immobilizing biologically active substances (proteins such as antibodies, enzymes, etc.; antigens; medications; etc.) by adsorption or covalency; depending on the nature of the active substance, it is possible to obtain a support capable of being advantageously employed in diagnostic tests, such as agglutination, radioimmunological assay ("RIA"), immunoradiometric assay ("IRMA"), enzyme immunoassay ("EIA"), and in affinity chromatography, as an enzyme catalyst in biotechnology, or as a cell culture support.

Another subject of the present invention is the biologically active support comprising:

a porous, water-insoluble inorganic matrix and particles of water-insoluble polymer on the surface of the said matrix, the polymer being "sensitized" by an effective quantity of biologically active substances.

The quantity of "sensitizing" substance which is present is generally in the order of about 0.1 to 15% by weight relative to the weight of the polymer particles. This quantity is chosen as a function of the required application of the biologically active support.

Particles of a polymer "sensitized" by biologically active substances means polymer particles onto which the active substances are fixed by adsorption or covalency.

The nature and the characteristics of the matrix, as well as the nature and the characteristics of the polymer particles have already been given above.

Among the "sensitizing" biologically active substances there may be mentioned proteins such as antibodies, enzymes and antigens, medications, etc.

The biologically active supports which are the subject of the present invention may be prepared by "deposition" of the particles of a polymer "sensitized" by biologically active substances on the surface of the matrix merely by contact of an aqueous dispersion (latex) of particles of a polymer "sensitized" by biologically active substances, with the porous matrix, followed by drying at a temperature which is compatible with the biologically active substance fixed onto the particles. Optionally, the matrix may be washed after deposition and prior to drying.

The "sensitization" of the polymer particles by the biologically active substance may be carried out by adsorption or else by coupling. The coupling reaction involves the fixing of the reactive or functional groups of the biological molecule..

The coupling reaction may be carried out according to well-known methods. For example it is known to make use of coupling agents (such as glutaraldehyde, water-soluble carbodiimide, N-hydroxybenzotriazole, spacers of the 1,6-diaminohexane type, polysaccharide, etc.) by activation of the polymer functional groups, (for example by diazotization, by reaction with cyanogen bromide, with tosyl chloride, etc.) followed by reaction with the molecule to be fixed.

Examples of coupling reactions are given in U.S. Pat. Nos. 3,857,931, 4,045,384, 4,140,662, 4,046,723 and 4,421,896, British Patent No. 2,004,892, French Patents Nos. 2,331,567, 2,345,459 and 2,378,094, and European Patent No. 15,841, etc.

An embodiment of the process for the preparation of the said biologically active supports consists in "depositing" the particles of "unsensitized" polymer on the surface of the matrix according to the process described above relating to the supports for biologically active molecules and then fixing the biologically active molecules onto the polymer particles by adsorption or coupling according to the methods described above.

The biologically active supports forming the subject of the invention may be employed, depending on the nature of the active substance immobilized on the polymer particles, in diagnostic tests (RIA, IRMA, immunoradiometric and EIA), in affinity chromatography, as an enzyme catalyst in biotechnology, and as a cell culture support.

They are of particular interest as diagnostic tests when the immobilized active substance is an immunoreagent (antigen or antibody). In particulate form, the said supports may form the packing of columns and in particular of capillary tubes which can be employed for producing qualitative or semi-quantitative tests.

The following examples are given by way of indication and cannot be considered as a limit on the scope or on the spirit of the invention.

EXAMPLE 1

Preparation of a Latex of "Sensitized" Polymer Particles

Fragments of antiprotein C rabbit antibody F (ab')$_2$ are incubated at a concentration of 1 mg/l in a saline phosphate buffer at pH 7.8 in the presence of an Estapor K 025 latex marketed by Rhone-Poulenc (calibrated latex consisting of polystyrene microspheres 0.25 microns in diameter), at a concentration of 1% by weight of polymer particles in the buffer.

After 17 hours of incubation at 22° C. the sensitized latex is washed three times with water, is centrifuged and is then redispersed in a gelatin phosphate buffer at a concentration of 1% by weight of polymer particles in the buffer.

Deposition of the Particles of "Sensitized" Polymer onto a Porous Silica

Spherosil X 005 silica marketed by I B F (silica particles 100 to 200 microns in diameter with a pore volume of 1 ml/g, a pore diameter of 0.30 microns and a specific surface area of 10 m$^2$/g are added thereto as a fine shower and with gentle stirring, in a proportion of 10% by weight relative to the weight of the dispersion (that is 1,000% by weight relative to the weight of the particles).

After 2 hours' impregnation at rest and at ambient temperature, the silica is washed five times with distilled water and is then dried in the oven at 50° C. for two hours.

Preparation of a Capillary Test

A capillary tube of the Pasteur pipette type is closed at its lower end with a plug of cotton wool. The capillary part of the tube is filled to a depth of 5 cm with the silica previously prepared under vibration using an agitator of the Reax 2000 type, marketed by Prolabo.

The upper end of the capillary tube is closed with a cotton wool plug.

Qualitative Diagnostic Test (Sandwich Method)

The lower end of the capillary tube is immersed in an aqueous solution of protein C (antigen).

The silica column is filled in less than 5 minutes. The tube is incubated for 2 hours at ambient temperature. The tube, fitted with a suction medicine dropper is immersed in a wash solution (Tween phosphate buffer) and is then inverted to remove the washing water.

The tube, fitted with its reduced-pressure medicine dropper, is then immersed in an aqueous solution of antiprotein C-peroxidase antibody until the support is completely impregnated.

After incubation for two hours at ambient temperature followed by washing as before, a solution of ABTS substrate (based on 2,2'-azinodi-3-ethylbenzthiazoline sulphate) discloses the presence of protein C as a blue-green colouring of the silica.

EXAMPLE 2

Reactants Employed silica: Spherosil X 005 latex: Estapor K1 - 010 (microspheres of carboxylated polystyrene containing 443 microeq. —COOH functional groups per g and with a diameter of 0.175 microns).

antibody: antirabbit Ig G horseradish peroxidase, marketed by Amersham coupling reagent: 3-dimethylaminopropylcarbodiimide (C D I) marketed by Aldrich buffer: MES at pH 5.5 (0.05 M/l aqueous solution of morpholinoethanesulphonic, marketed by Merck)

substrate: ABTS (1 mM/l aqueous solution of 2,2'-azinodi-3-ethylbenzthiazoline sulphate)

stabilizer: 0.1 M/l aqueous solution of citric acid containing 0.01% by weight of $NaN_3$.

Deposition of the Polymer onto Silica

The latex at the initial concentration of 10% by weight is diluted with distilled water to a concentration of 0.5% by weight.

10% by weight of silica (based on the diluted latex) is added to the diluted latex; this addition is carried out as a fine shower for 10 seconds under ultrasound.

The mixture obtained is based on a slowly rotating roller (approximately 1 rpm) for 3 hours and is then stored at ambient temperature for 1 night.

The product obtained is washed with 5 times 100 ml portions of distilled water per gram of silica, and is then dried for 24 hours at 45° C.

Sensitization 1 g of the product prepared above is introduced into 10 ml of a solution containing 1 mg/ml of CDI coupling reagent in distilled water.

After incubation for 30 minutes at 50° C., the product obtained is washed with 3 10-ml portions of MES buffer and is then brought into contact with 5 ml of a solution containing 10 mg/ml of peroxidase antibody in MES buffer.

After incubation for 90 minutes at 37° C., the biologically active support thus obtained is washed with 3 20-ml portions of MES buffer. A suspension of biologically active support is thus obtained.

Determination

The fixed antibody is determined by optical density measurement in an Elisa Minireader II spectrophotometer (marketed by Dynatech).

The apparatus is calibrated as follows with solutions of peroxidase antibody in decreasing concentration (ranging from 0.25 mg/ml to 0.03 mg/ml) in MES buffer.

100 microliters of peroxidase antibody solutions are placed in the wells of the Elisa microplate and 100 microliters of ABTS solution are added. After 10 minutes' incubation at ambient temperature 50 microliters of a 0.1M aqueous solution of citric acid containing 0.01% by weight of $NaN_3$ are introduced into each well to stop the reaction, before the optical densities are measured. The calibration straight line is shown in FIG. 1.

An optical density measurement is carried out under the same conditions on the supernatant of the suspension of biologically active support obtained in the sensitization operation. The value obtained is in the order of 0.15, which, according to FIG. 1, corresponds to a quantity of free antibodies of less than 0.03 mg/ml (which will be taken into account in the calculation of the number of antibodies fixed onto the support).

A 0.5-ml sample of biologically active support suspension prepared in the sensitization operation is taken, and this sample is placed in a small tared tube.

0.5 ml of ABTS solution is added thereto; the mixture is incubated for 10 minutes at ambient temperature; the product released by the reaction of the antibody fixed on the support and the ABTS is transferred into solution. 200 microliters of supernatant are then placed in a well of the Elisa microplate with 50 microliters of 0.1M aqueous solution of citric acid containing 0.01% by weight of $NaN_3$.

The corrected optical density (after 0.15 has been deducted) is 1.52 which, according to FIG. 1, corresponds to 0.217 mg/ml of antibody, that is 0.05425 mg of antibody per 250 microliters of suspension (200 microliters of supernatant+50 microliters of stabilizing solution).

The support is separated from the liquid medium and is then placed in the oven at 80° C. for 24 hours, and is weighed.

Its mass is 0.03155 g.

The quantity of antibody fixed per gram of silica is therefore 0.05425/0.03155=1.719 mg/g.

EXAMPLE 3

The operation described in Example 2 is repeated in the same conditions, starting from:

Estapor $A_1$-005 latex (microspheres of styreneacrylate copolymer containing 444 microeq. —COOH functional groups per g and with a diameter of 0.07 microns).

The corrected optical density is 1.65, which corresponds to 0.237 mg/ml of antibody, that is 0.005925 mg of antibody per 250 microliters of suspension. The mass of the support is 0.01965 g. The quantity of antibody fixed per gram of silica is 3.015 mg/g.

EXAMPLE 4

Preparation of the Support

C.P.G.2® porous glass (marketed by Controlled Pore Glass with a pore diameter of 0.14 microns, a specific surface area of 0.13 $m^2/g$, a pore volume of 0.7 ml/g and a particle diameter of 125 microns) is added as a fine shower and with gentle stirring to an Estapor $A_1$-005 latex, namely 10% by weight relative to the weight of dispersion.

After 2 hours' impregnation at rest and at ambient temperature, the support obtained is washed five times with distilled water.

Sensitization

Fragments of antiprotein C rabbit antibody $F(ab')_2$ are left to incubate at a concentration of 1 mg/l in a saline phosphate buffer at pH 7.8 in the presence of the support suspension prepared above, at a concentration of 1% by weight of dry support in the buffer.

After 17 hours' incubation at 22° C., the sensitized support obtained is washed three times with water and is then separated from the liquid medium and dried in the oven at 50° C. for 2 hours.

A capillary test can be prepared according to the process of Example 1.

What is claimed is:

1. A support for biologically active molecules, comprising:

a particulate, non-fibrous, porous, water-insoluble inorganic matrix, said matrix being in the form of particles with an approximate diameter in the range of about 4 μm to 5 mm and having a pore volume in the range of about 0.5 to about 1.8 ml/g, a pore diameter in the range of about 0.005 to about 10 microns and a specific surface area in the range of about 2 to about 1,000 m$^2$/g; and water-insoluble polymer particles on a surface of said matrix which are capable of fixing biologically active molecules, the diameter of said water-insoluble polymer particles being smaller than the diameter of the pores of the matrix.

2. The support as claimed in claim 1, wherein the matrix comprises a material selected from the group consisting of silica, alumina or porous glass.

3. The support as claimed in claim 1, wherein the weight of the matrix is approximately 1 to 1,000 times that of the total weight of the water-insoluble polymer particles thereon.

4. The support as claimed in claim 1, wherein the water-insoluble polymer is derived from a vinylaromatic monomer, an alkyl ester of an α, β-unsaturated acid, an ester of an unsaturated carboxylic acid, vinyl chloride, vinylidene chloride, a conjugated diene, an unsaturated monomer containing a nitrile functional group or a siloxane.

5. The support as claimed in claim 1, wherein the water-insoluble polymer is derived from a water-immiscible monomer and contains less than 10% of at least one comonomer containing an ionizable or reactive group.

6. The support as claimed in claim 5, wherein the comonomer is vinylbenzene sulphonate, a sulphoalkyl ester of an unsaturated acid, an unsaturated carboxylic acid, a hydroxyalkylacrylate or methacrylate, an aminoalkyl ester of an unsaturated acid, acrylamide, vinylbenzene chloride or glycidyl methacrylate.

7. The support as claimed in claim 1, wherein the matrix surface has functional groups capable of reacting covalently with the polymer particles.

8. A biologically active support formed from the support for biologically active molecules claimed in claim 1, wherein the water-insoluble polymer particles are sensitized by a biologically active substance.

9. The biologically active support as claimed in claim 8, wherein the biologically active sensitizing substances are proteins, antigens or medications.

10. The biologically active support as claimed in claim 9, wherein the quantity of sensitizing substance is in the range of from about 0.01 to 15% by weight relative to the total weight of the water-insoluble polymer particles.

11. A support as in claim 1, wherein said pore diameter is in the range of 0.1 to 1 μm.

12. A support as in claim 1, wherein said diameter of the particles forming said matrix is in the range of 50 to 500 μm.

13. A support as in claim 1, wherein the weight of the matrix is 50 to 500 times the weight of the water-insoluble polymer particles.

14. A process for the preparation of a biologically active support comprising contacting biologically active molecules with a support which forms the subject of one of claims 1, 2, 3–7 and 11–13, and fixing the biologically active molecules onto the water-insoluble polymer particles on the surface of the matrix of the support.

* * * * *